United States Patent [19]
Kato et al.

[11] 3,936,459
[45] Feb. 3, 1976

[54] 1',4'-DIHYDRO-1-METHYL-SPIRO [PIPERIDINE AND PYRROLIDINE-2,3'(2'H)QUINOLINE]-2'-ONE COMPOUNDS

[75] Inventors: Hideo Kato; Eiichi Koshinaka, both of Fukui, Japan

[73] Assignee: Hokuriku Pharmaceutical Co., Ltd., Katsuyama, Japan

[22] Filed: Dec. 11, 1974

[21] Appl. No.: 531,452

[30] Foreign Application Priority Data
Dec. 19, 1973 Japan.............................. 48-141177

[52] U,S, Cl.... 260/288 CE; 260/239 BD; 260/288 CF; 260/289 K; 424/258
[51] Int. Cl.$^2$............... C07D 215/38; C07D 215/22
[58] Field of Search..... 260/288 CE, 288 CF, 289 K

[56] References Cited
OTHER PUBLICATIONS
Fieser et al.; Advanced Organic Chemistry, (1961), pp. 740–741.

*Primary Examiner*—Donald G. Daus
*Assistant Examiner*—Mary C. Vaughn
*Attorney, Agent, or Firm*—Burgess, Ryan and Wayne

[57] ABSTRACT

Spiro compounds having the structural formula

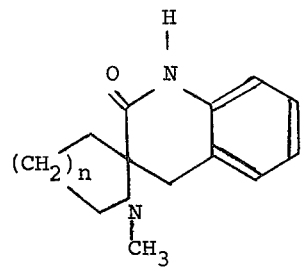

where *n* is an integer of 1 or 2, are disclosed. These compounds are useful as analgetic, antihistamine and spasmolytic agents. They are indicated in the management of conditions such as headache, seasonal allergies and the like.

3 Claims, No Drawings

1',4'-DIHYDRO-1-METHYL-SPIRO [PIPERIDINE AND PYROLIDINE-2,3'(2'H)QUINOLINE]-2'-ONE COMPOUNDS

The present invention relates to novel spiro-compounds having pharmaceutical activities as well as a novel process for their production. More particularly, the present invention relates to novel spiro-compounds of the formula:

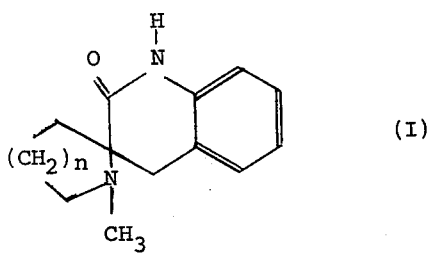

(I)

wherein $n$ is an integer of 1 or 2, and the corresponding pharmaceutically acceptable acid addition salts.

According to the present invention, compounds of the formula (I) supra are produced by treating a benzodiazepinium halide derivative of the formula:

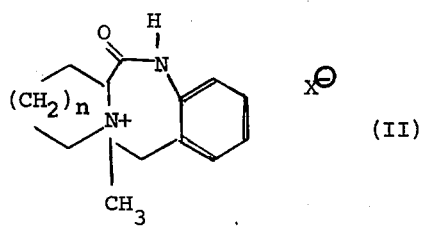

(II)

wherein $n$ is as defined above, and X is a halogen atom such as chlorine, bromine, fluorine or iodine, with phenyllithium (Ph-Li) employing the method known as "Stevens Rearrangement." See *J. Chem. Soc.* 1928, 3193; 1930, 2107 and 1932, 55, 1926, 1932.

It has been found that after studying ring open reactions of compounds of the formula (II), the spiro compounds (I) can be formed with phenyllithium.

Accordingly, the present invention is carried out by reacting a compound of the formula (II) with a solution containing an excess of phenyllithium.

As reaction solvents, illustratively, anhydrous ether or an anhydrous ether-tetrahydrofuran mixture may be suitably employed. The reaction may be suitably carried out at room temperature, i.e., from about 15° to 25°C. An adequate amount of phenyllithium is suitably from 3 to 5 moles per mole of compound (II).

The products (I) in accordance with the present invention can be converted into the corresponding salts using pharmaceutically acceptable inorganic or organic acids by methods known in the art. Specific examples of these acids include hydrochloric acid, hydrobromic acid, sulfuric acid, maleic acid, fumaric acid, oxalic acid, tartaric acid, citric acid, succinic acid, and the like.

Compounds of the formula (I) and the salts thereof exhibit analgetic, anti-histamic and spasmolytic activities and vasoconstrictor effects on the circulatory system in a mammal. They are indicated in the management of conditions such as headache, minor muscular pain or seasonal allergies such as hay fever. A dose of 5 to 25 mg/kg orally or by injection 2 to 3 times daily is suggested. This dose regimen can be varied. Additionally, the present compounds are useful as intermediates for the production of other pharmaceutical agents.

The invention will now be illustrated by the following examples.

Example

1', 4'-Dihydro-1-methyl-spiro[piperidine-2,3'(2'H) quinolin]-2'-one

To a solution of Ph-LI in Et$_2$O prepared from 0.35g Li and 4.70g PhBr was added 1.8g of 11-methyl-5,6,6a,7,8,9,10,12-octahydro-6-oxo-pyrido (2,1-C) (1,4) benzodiazepinium iodide in small portions.

Thereafter, THF was added and the reaction mixture was stirred at room temperature for 16 hours, and evaporated.

The residue was dissolved in 10% HCl, and the aqueous layer was washed with Et$_2$O, made alkaline with K$_2$CO$_3$ and extracted with CHCl$_3$.

The CHCl$_3$— layer was washed with H$_2$O, dried and evaporated. The residue was purified through a silica gel-column (CHCl$_3$:MeOH=4:1) to obtain the desired product which was recrystallized from iso-Pr$_2$O. mp.157°–159°C.

Elemental Analysis C$_{14}$H$_{18}$ON$_2$

Calcd. C:73.01; H:7.88; N:12.17, Found: C:72.80; H:8.00; N:11.85.

The following compound was obtained in a similar manner. i) 1',4'-Dihydro-1-methyl-spiro[pyrrolidine-2,3'(2'H)quinolin]-2'-one mp. 129°–130°C after recrystallization from (iso-Pr$_2$O).

What is claimed is:
1. A spiro compound of the formula:

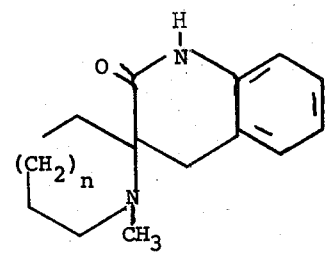

wherein $n$ is an integer of 1 or 2, and the corresponding pharmaceutically acceptable acid addition salts thereof.

2. A spiro compound according to claim 1 which is 1',4'-dihydro-1-methyl-spiro[piperidine-2,3'(2'H) quinolin]-2'-one.

3. A spiro compound according to claim 1 which is 1',4'-dihydro-1-methyl-spiro[pyrrolidine-2,3'(2'H)- quinolin]-2'-one.

* * * * *